United States Patent [19]

Spence

[11] Patent Number: 4,783,321

[45] Date of Patent: Nov. 8, 1988

[54] STERLIZATION CONTAINER SYSTEM

[75] Inventor: Jerry L. Spence, Redmond, Wash.

[73] Assignee: Instrumed, Inc., Kirkland, Wash.

[21] Appl. No.: 806,288

[22] Filed: Dec. 6, 1985

Related U.S. Application Data

[63] Continuation-in-part of Ser. No. 684,745, Dec. 18, 1984, abandoned.

[51] Int. Cl.⁴ ............................ A61L 2/06; A61L 2/20
[52] U.S. Cl. ..................................... 422/300; 422/297; 206/439; 220/324; 220/371; 220/DIG. 27; 55/385.4
[58] Field of Search ................. 422/26, 119, 297, 300; 436/1, 93; 206/364, 365, 366, 368, 438, 439, 509; 220/24, 315, 324, 371, 378, 372, DIG. 27; 55/385 C, 501, 503, 505, 511; 292/113

[56]    References Cited

U.S. PATENT DOCUMENTS

| | | | |
|---|---|---|---|
| 2,384,398 | 9/1945 | Raven | 422/300 |
| 3,252,580 | 5/1966 | Getzin | 55/503 |
| 3,259,411 | 7/1966 | Griffiths | 292/113 |
| 3,957,469 | 5/1976 | Nebash | 55/503 |
| 3,966,439 | 6/1976 | Vennos | 55/501 |
| 4,194,622 | 3/1980 | Lewis | 422/34 X |
| 4,244,920 | 1/1981 | Manschot et al. | 422/102 |
| 4,318,557 | 3/1982 | Bourne et al. | 292/113 |
| 4,331,257 | 5/1982 | Taschner | 220/324 |
| 4,358,908 | 11/1982 | Song | 47/66 |
| 4,372,921 | 2/1983 | Sanderson et al. | 422/300 |
| 4,382,808 | 5/1983 | Van Wormes, Jr. et al. | 55/503 |
| 4,416,417 | 11/1983 | Sanderson et al. | 422/300 |
| 4,481,797 | 11/1984 | Milo | 220/318 |
| 4,487,606 | 12/1984 | Leniton et al. | 55/385 C |
| 4,510,119 | 4/1955 | Heney | 422/102 |
| 4,512,498 | 4/1985 | Leibinger | 422/310 X |
| 4,514,361 | 4/1985 | Hirsch | 422/119 X |
| 4,617,178 | 10/1986 | Nichols | 422/300 |

FOREIGN PATENT DOCUMENTS 2375869  7/1978  France ......................... 422/300
908407  10/1962  United Kingdom .............. 220/371

OTHER PUBLICATIONS

Portions of the Sep.–Oct. 1984 issue of the Journal of Hospital Supply, Processing, and Distribution, pp. 26–31 and Jarit ad, American ad(2p), Genesis ad, and Amsco ad (2p).

Primary Examiner—Michael S. Marcus
Assistant Examiner—Jill Johnston
Attorney, Agent, or Firm—Gregory W. Moravan

[57]    ABSTRACT

A sterilization container system for sterilizing surgical instruments, having a lid secured to a base by latches. The latches are automatically disengaged when the latches' release arms are raised to form handles by which the lid can be easily and securely manipulated; while the latches are automatically engaged when the latches' release arms are lowered, sealing the lid to the base. The base is provided with an outer safety wall, which is lower than and which extends around the base's inner wall, in order to help protect the top of the base's inner wall from inadvertent contamination when the lid is removed. Disposable paper filters are sealed over the vents inside the lid and base by cooperating filter paper sealing flanges provided in the filter papers' retainers, lid and base, in order to maintain the sterility of the contents of the sterilization container system after sterilization. Dual disc filter paper retainers provide non-aligned vents which prevent tearing or puncturing of the filter papers by the instruments being sterilized. Alignment cams on the base ensure proper alignment of lid and base for a good seal therebetween. The instrument basket inside the sterilization container system has a base elevated above the filter paper retainer to permit free circulation of the sterilizing media. Support feet on the base elevate the instrument basket above the bottom of the base to prevent condensation from being trapped within the sterilization container system.

10 Claims, 6 Drawing Sheets

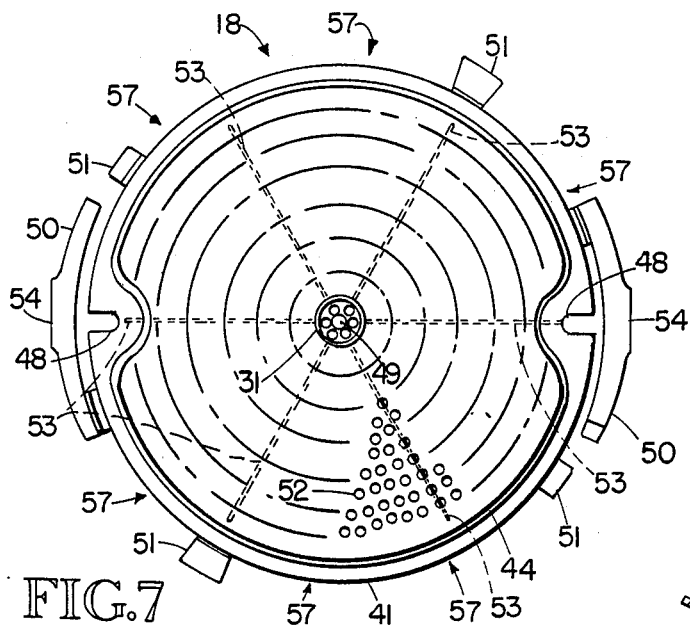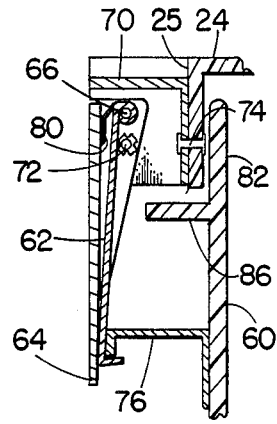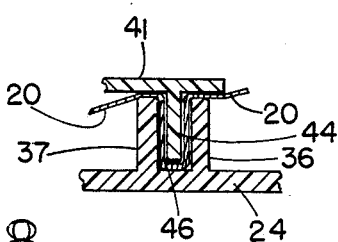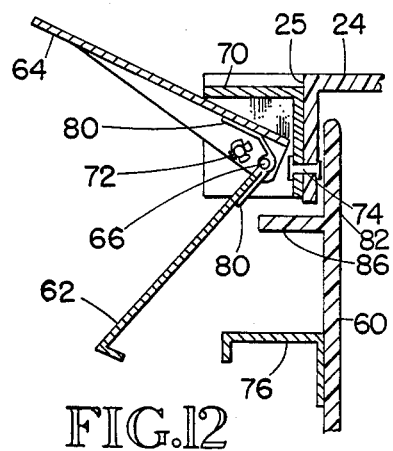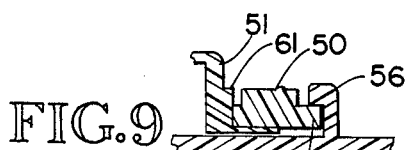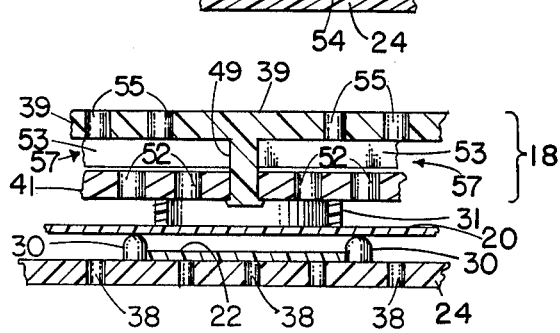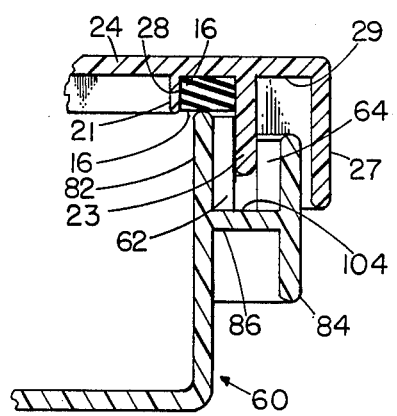

4,783,321

STERILIZATION CONTAINER SYSTEM

This application is a continuation-in-part of U.S. patent application Ser. No. 684,745 filed Dec. 18, 1984 and now abandoned.

BRIEF SUMMARY OF THE INVENTION

The present invention relates to container systems, and in particular relates to a sterilization container system which is adapted to hold medical instruments, for example, while they are being sterilized, and which is adapted to retain them in a sterile condition until needed after sterilization is complete.

In basic form, the sterilization container system of the present invention comprises a lid secured to a base with latches, so when the lid is removed, the medical instruments may be placed in or removed from the sterilization container system. Vents in the lid and base of the sterilization container system permit the free circulation of sterilization media, such as steam, through the sterilization container system during any conventional sterilization process. Filter paper is sealed inside the sterilization container system over the vents, and a seal is provided between the lid and the base in order to not only keep the sterilized medical instruments inside the sterilization container system sterile, but to also prevent soiled medical instruments held by the sterilization container system after the surgery is complete from contaminating the environment around the sterilization container system until the soiled medical instruments can be cleaned and resterilized.

Another object of the invention is to provide a sterilization container system in which removing, handling, and replacing the lid is made easier, more convenient, and more secure. This is done not only for convenience, but also for aiding in protecting against the inadvertent contamination of the sterilized medical instruments in the sterilization container system by the lid or the user's hands when the lid is removed and manipulated in order to permit removal of the sterilized medical instruments for use. This object is achieved by providing latches for the lid whose release arms, as they are rotated up and out to their extended positions from their latched positions, not only automatically disengage the latching arms, but also automatically form handles, when they are fully extended, by which the lid can be more securely lifted, lowered and manipulated.

An additional object of the invention is to provide a sterilization container system which reduces the changes of inadvertently contaminating sterilized medical instruments as they are being removed from the sterilization container system. This object is achieved by providing an outer protective wall around the peripheral lip of the inner wall of the base of the sterilization container system. The outer protective wall helps to prevent non-sterile objects from contacting, and thus contaminating, the inner wall's peripheral lip once the lid of the sterilization container system is removed. Thus, if the sterile medical instruments bump the peripheral lip of the inner wall as they are being removed from the sterilization container system, there is less chance they will be contaminated since the outer protective wall helps prevent the inadvertent contamination of the peripheral lip of the inner wall by contaminated objects once the lid of the sterilization container system has been removed. Preferably, the upper lip of the outer protective wall is slightly lower than the peripheral lip of the inner wall, to reduce the chance that the sterilized instruments might contact, and be contaminated by, the non-sterile upper lip of the outer protective wall as they are being removed from the sterilization container system.

Further objects of the invention are to provide a sterilization container system in which the periphery of the filter paper over its vents is sealed, to help prevent contamination from entering or leaving the sterilization container system; in which the filter paper is quickly, easily, and accurately secured in place when being installed; in which the filter paper is quickly and easily removed when being discarded after use; and in which the installed filter paper is protected, to help prevent any punctures or tears of the filter paper which might permit contamination to pass through it.

These objects are achieved through providing multi-purpose filter paper retainers which cooperate with associated structures inside the sterilization container system's lid and base. To provide the desired sealing of the periphery of the filter paper, the filter paper retainers and the sterilization container system's lid and base are provided with interlocking flanges which tightly sandwich the periphery of the filter paper between them when the filter paper retainers are assembled to the lid and base, thereby sealing the filter paper over the vents in the lid and base.

To provide for quick, easy and accurate installation of the filter paper, alignment holes are provided in the filter paper and filter paper retainers which register with alignment pins provided in the sterilization container system's lid and base.

To provide for the quick and easy removal of the installed filter paper, the filter paper is provided with tabs which are elevated by corresponding support pins provided in the sterilization container system's lid and base. The locking mechanisms for each filter paper retainer are arranged so that as their locking arms are pressed by the fingers of the user to disengage them, the elevated tabs on the filter paper are simultaneously easily engaged by the fingers, so that when the filter paper retainer is lifted away, the used filter paper may be automatically lifted away also.

To provide for protection of the installed filter paper from being torn or punctured during use, which might result in the instruments being contaminated, the sealed portion of the filter paper is completely covered on one side by the sterilization container system's lid or base, and on the other side by its filter paper retainer. The vent holes provided in the lid and base are small and deep enough to help protect the filter paper from accidental contact by foreign objects outside the sterilization container system which might puncture or tear the filter paper, and yet they are also numerous enough to provide for the desired free passage of the sterilizing media through the sterilization container system during the sterilization process.

To help protect the installed filter paper from being torn or punctured by the instruments inside the sterilization container system, a unique double disc filter paper retainer is utilized. Each disk has numerous holes to permit the passage of the sterilizing media therethrough. However, the holes in the two discs are arranged so that when the filter paper retainer is installed they are out of registry, thereby preventing the instruments inside the sterilization container system from tearing or puncturing the filter paper. In addition, spacing ribs located between the discs provide side venting between the discs to further allow the free passage of the sterilizing media through the filter paper retainer while still preventing the instruments inside the sterilization container system from tearing or puncturing the filter paper.

A further object of the invention is to provide a highly visible, easily replaceable indicator material on the inside of the sterilization container system which will visually indicate, as by a change in color, that the sterilization container system and its contents have been properly sterilized. This object is achieved by providing retaining pins on the inside of the lid of the sterilization container system which are sized and spaced to retain the indicator material adjacent the vent holes in the lid, and to permit its easy insertion and removal. Since the indicator material is retained adjacent the lid's vent holes, it is easily seen through the lid's vent holes from the outside of the sterilization container system. Alternatively, the indicating material may be carried by the filter paper, where it can be seen through the lid's vent holes.

Another object of the invention is to provide stacking ridges on the corners of the outside of the lid of the sterilization container system, and cooperating stacking angles on the corners of the outside of the base of the sterilization container system which aid in stacking a plurality of sterilization container systems on top of each other.

Typically, a removable, perforated basket is used to conveniently hold the instruments inside the sterilization container system while they are being sterilized. Further objects of the present invention are to help ensure the basket does not interfere with the free circulation of the sterilizing media inside the sterilization container system and to help ensure that any condensation (as when steam is the sterilizing media) is not trapped inside the sterilization container system by the basket. These objects are achieved by providing the basket with a bottom which is elevated clear of the filter paper retainer. Support feet provided on the inside of the base of the sterilization container system hold the lower rim of the basket above the inside of the base to permit any condensation to flow freely underneath the basket, and thus help prevent condensation from being trapped inside the sterilization container system by the basket.

Another object of the present invention is to help ensure proper alignment of the lid with the base so that the sealing lip on the base makes proper contact with the sealing gasket in the lid. This object is achieved by providing alignment ridges on the base which contact certain portions of the lid to properly align the base and lid.

Although the sterilization container system has been described above as being used with medical instruments, such description was, of course, merely by way of non-limiting example since the sterilization container system can be used with anything needing sterilization.

The foregoing is intended to be but a brief summary of, not a detailed catalog of, the objects, features, advantages and characteristics of the present invention, since these and further objects, features, advantages and characteristics of the present invention will be either expressly or inherently disclosed herein.

BRIEF DESCRIPTION OF THE DRAWINGS

FIG. 7 is a plan view of the reverse side of the assembled filter paper retainer seen in FIGS. 2 and 3;

FIG. 8 is a cross-sectional view taken along line 8—8 of FIG. 6;

FIG. 9 is a cross-sectional view taken along line 9—9 of FIG. 6;

FIG. 10 is a cross-sectional view taken along line 10—10 of FIG. 6;

FIG. 11 is a cross-sectional view taken along line 11—11 of FIG. 1, showing the lid latching mechanism closed, with some nearby parts of the sterilization container system not shown, for clarity;

FIG. 12 is a view like that of FIG. 11, except the lid latching mechanism is shown open;

FIGS. 13 and 14 are cross-sectional views taken along line 13—13 of FIG. 1 and line 14—14 of FIG. 6, respectively;

DETAILED DESCRIPTION OF THE INVENTION

Figure 1:
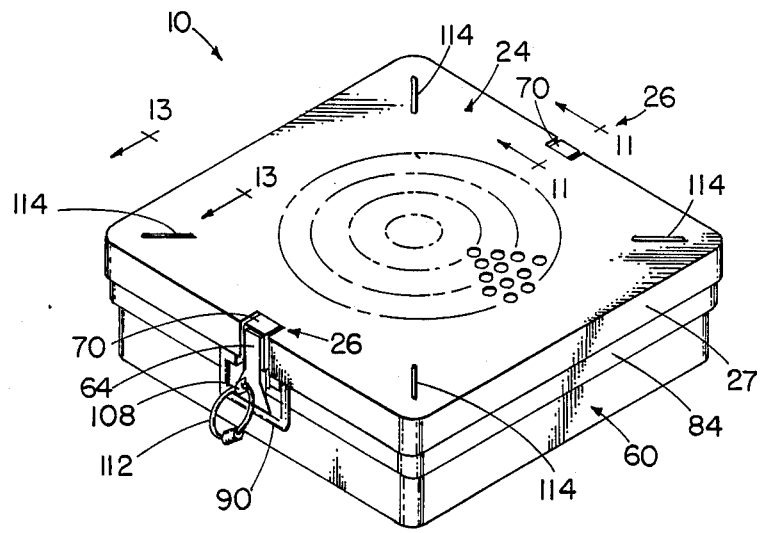
FIG. 1 is a perspective view of the sterilization container system of the present invention.

Turning now to the Figures, the sterilization container system 10 of the present invention is shown assembled in FIG. 1. The sterilization container system 10 comprises two main assemblies—a lid assembly 12, seen inverted for clarity in FIG. 2; and a base assembly 14, seen in FIG. 3.

LID ASSEMBLY

The lid assembly 12 comprises seven main components, namely a gasket 16, a filter paper retainer 18, a filter paper 20, an indicator material 22, a lid 24, and two latch assemblies 26.

Figure 6:
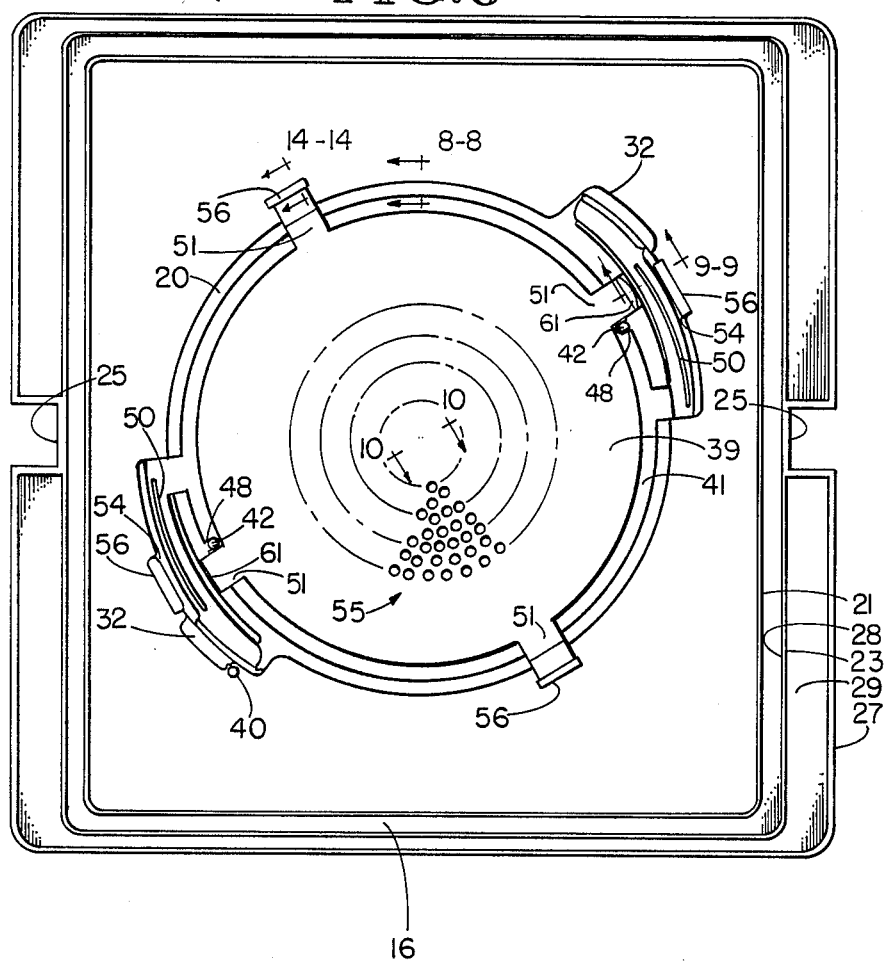
FIG. 6 is a bottom plan view of the lid assembly when assembled, with certain portions broken away for clarity, and with the handle-latch assemblies not shown for clarity.

Gasket 16 is received and held in the lid's gasket channel 28 which is sized to snugly receive it. Gasket 16 may be secured in place by a friction fit and/or by the use of any compatible adhesive which will withstand the contemplated sterilization conditions. Gasket 16, when installed in gasket channel 28, forms a closed figure as seen in FIG. 6. Gasket 16 is formed from FC7504HS silicone grey sponge, closed cell, medium density, made by the J-Bar Selene Corp., located in Michigan.

Figure 2:
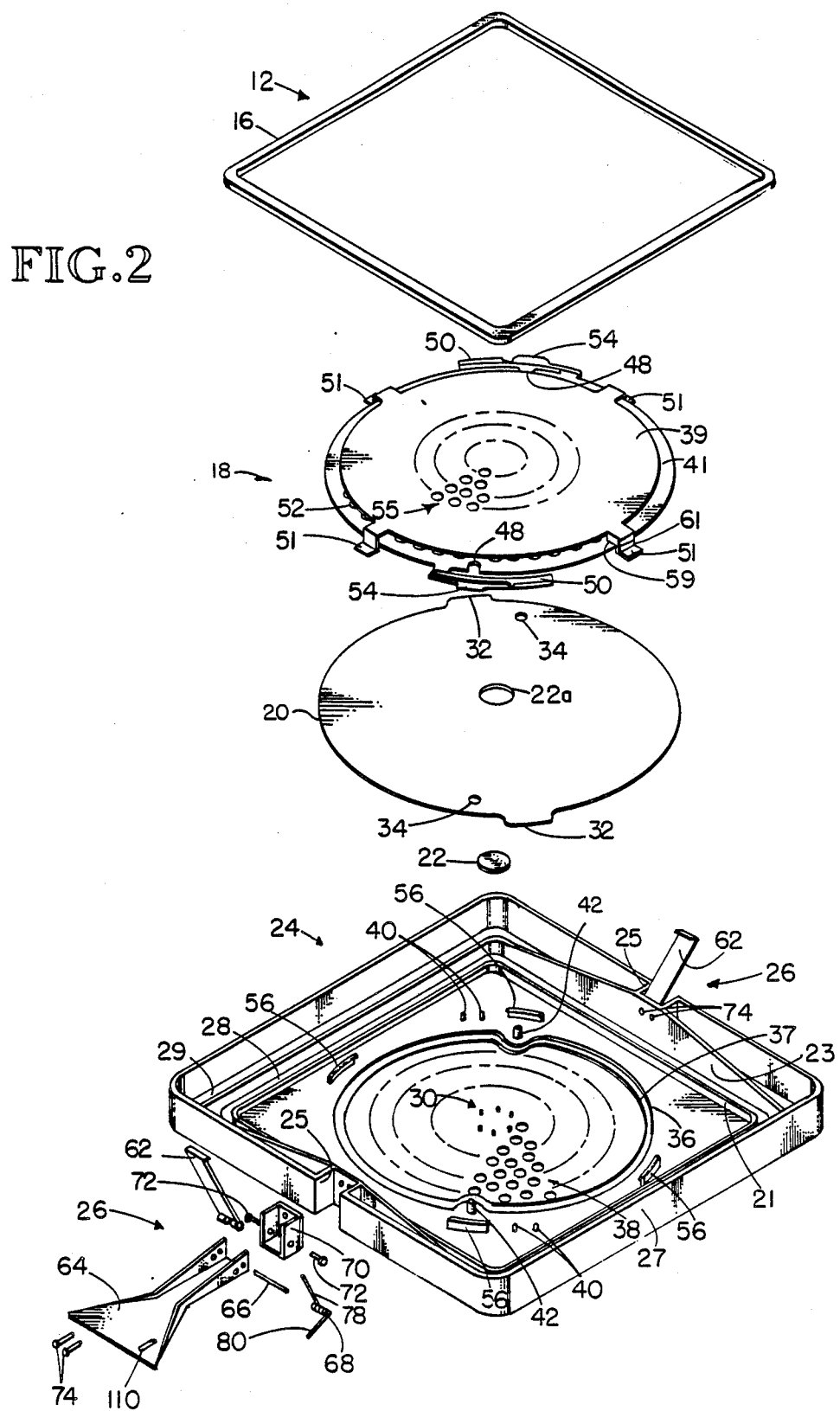
FIG. 2 is an inverted exploded perspective view of its lid assembly.

Gasket channel 28, as seen in FIGS. 2, 6 and 13, is defined by inner wall 21 and outer wall 23 of lid 24. Outer wall 23 of gasket channel 28 is made taller on the sides of lid 24 having latch mounting recesses 25, as seen in FIG. 2, for strength in supporting latch assemblies 26. The outer periphery of lid 24 terminates in an outer wall 27 which defines a pair of latch mounting recesses 25. An outer channel 29 of lid 24 is defined between lid walls 23 and 27. As seen in FIG. 13, the bases of lid walls 21, 23 and 27 are coplanar. Lid walls 21, 23 and 27 help to make lid 24 strong and rigid.

Indicator materials 22 is releasably held by a friction fit by retaining pins 30 on the inner surface of lid 24, as seen in FIGS. 2 and 10; 6 retaining pins 30 being illustrated, by way of non-limiting example. As seen in FIG. 10, when filter paper 20 is installed in lid 24, filter paper 20, filter paper retainer 18, and retaining disc 31 of filter paper retainer 18 hold indicator material 22 in place even if it became detached from retaining pins 30. Indicator material 22 is composed of any conventional media which indicates, as by a color change, that it (and thus the sterilization container system and its contents) have been exposed to proper sterilization conditions. By way of non-limiting example, indicator material 22 may be ink chemical dye, made by Eti/Tower Company located in Chicago, Ill.; and indicates sterility by changing color from white to brown when exposed to the following sterilization conditions: 250° F. steam (30 minutes at 18 pounds pressure), or ethylene oxide (140° F. for 12 hours). Naturally, visual inspection of indicator material 22 is easily done from outside of the sterilization container system 10 through vents 38 in lid 24.

Referring now to FIGS. 2 and 6, filter paper 20 has two tabs 32, two alignment holes 34 and may be any conventional sterilization filter media, such as Dex-Wrap/Grade #2359, made by the C. H. Dexter Company, located in Windsor Locks, Conn. Filter paper 20 is installed in lid 24 by laying it on lid 24 so it overlies lid filter paper sealing flanges (container sealing flange means) 36, 37 and lid vents 38, with its tabs 32 overlying support pins 40, and with alignment pins 42 on lid 24 extending through filter paper 20's alignment holes 34, as seen in FIGS. 2 and 6.

As seen, filter paper 20 may include an indicator area 22a. Indicator area 22a may be a piece of indicator material 22 affixed as by gluing to filter paper 20. Alternatively, indicator area 22a may be an area of filter paper 20 which has been impregnated or coated directly with any conventional indicator substance such as the active substance in conventional indicator strip 22 or such as ink chemical made by Tempil Corp., located in New York State, which will indicate, as by a color change, that the sterilization container system 10 and its contents has been properly sterilized. If such an indicator area 22a is provided for filter paper 20, then indicator material 22 and its retaining pins 30 could be eliminated since indicator area 22a would then be seen directly through vents 38 in lid 24.

A good seal is provided between filter paper 20 and the filter paper sealing flanges (container sealing flange means) 36, 37 of lid 24 when filter paper retainer 18 is installed in lid 24, as will be described below. This is because, as seen in FIG. 8, when the filter paper 20 and filter paper retainer 18 are installed on lid 24, the peripheral portion 46 of filter paper 20 is tightly sandwiched between the lid's filter paper sealing flanges (container sealing flange means) 36, 37, the filter paper retainer's filter paper sealing flange 44, and the adjacent portions of lid 24 and the lower disc 41 of filter paper retainer 18. Such a seal is important, as has been mentioned, to help prevent contamination of sterile surgical instruments inside sterilization container system 10; and if the sterilization container system is used to hold soiled surgical instruments after they have been used, it helps prevent the soiled instruments from contaminating the environment around sterilization container system 10. The filter paper sealing flanges (container sealing flange means) 36, 37, 44 on lid 24 and on the lower disc 41 of filter paper retainer 18, as seen in FIGS. 2, 3, 7 and 8, are sized to fit closely adjacent each other at all points when filter paper retainer 18 and lid 24 are assembled together, so the desired good seal is obtained completely about the peripheral portion 46 of filter paper 20.

Turning now to FIGS. 2, 3, 6, 7, 10, 15 and 16, filter paper retainer 18 includes an upper disc 39 and a lower disc 41 rotatably secured together by a pin 49. Lower disc 41 includes a pair of alignment holes 48, a pair of locking arms 50, and a plurality of vents 52 whose total area is chosen to permit the free and easy passage of the sterilizing media through filter paper retainer 18. Upper disc 39 includes four locking feet 51, six spacing ribs 53 and a plurality of vents 55 to permit the free and easy passage of the sterilizing media through filter paper retainer 18.

As seen in FIG. 10, when filter paper retainer 18 is assembled to lid 24 or base 14, the vents 52, 55 in its lower and upper discs are preferably located so they are completely unaligned. This important feature is to prevent the instruments which are inside the sterilization container system 10 from undesireably tearing or puncturing the filter paper 20, since it would be highly unlikely for an instrument to be able to pass through the completely unaligned vents 52, 55.

As seen in FIGS. 7 and 10 lateral vents 57 are provided between ribs 53 and upper and lower discs 39, 41. Thus the sterilizing media can freely enter the sterilization container system 10 through two routes through filter paper retainer 18. The first route is upward through vents 38, 52 and then through vents 55. The second route is upward through vents 38, 52 and then laterally outward through lateral vents 57. Here again it is seen that it would be highly unlikely for an instrument inside the sterilization container system 10 to be able to tear or puncture the filter paper 20 through the lateral vents 57.

As seen in FIGS. 6 and 9, filter paper retainer 18 is held in place by its resilient locking arms 50 whose locking lugs 54 releasably and resiliently engage corresponding locking ears 56 on lid 24. To install retainer 18, first its resilient locking arms 50 are manually urged towards the center of retainer 18 as retainer 18's alignment holes 48 are slipped over alignment pins 42 on lid 24. Once retainer 18 is in place, locking arms 50 are released, thereby resiliently urging their locking lugs 54 outwardly and into engagement with their corresponding locking ears 56 on lid 24.

Figure 14:
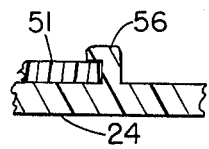
Figure 15:
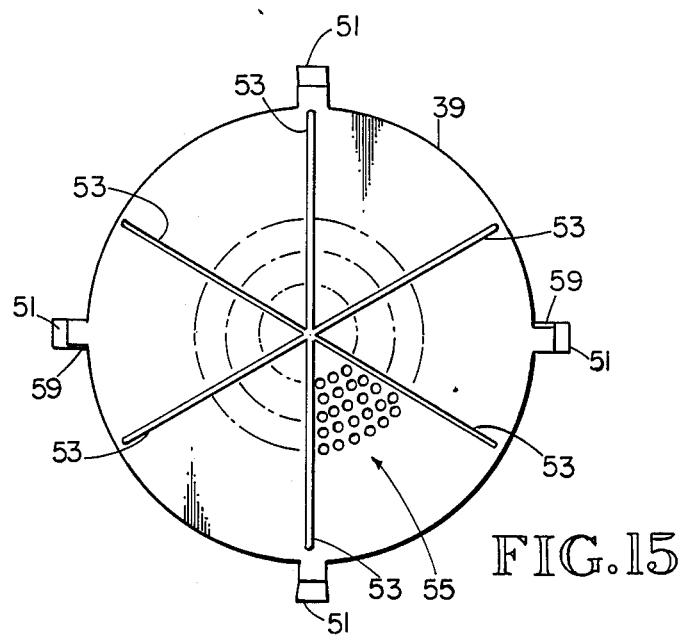
FIG. 15 is a bottom plan view of the upper disc of the filter paper retainer.
Figure 16:
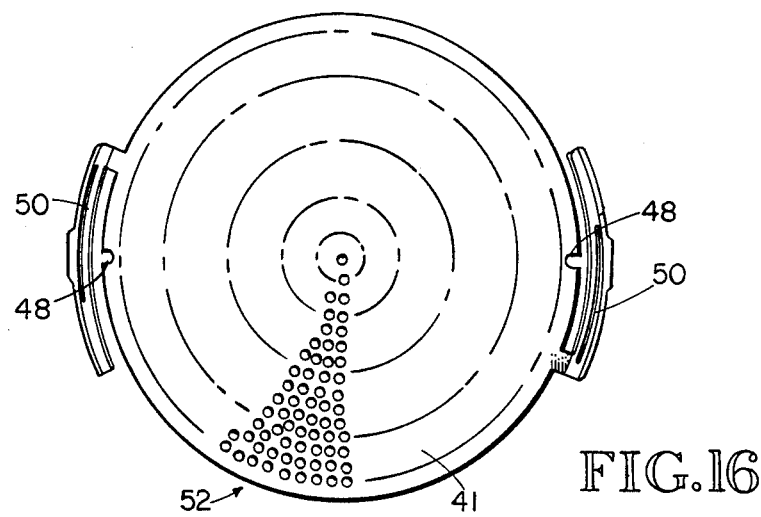
FIG. 16 is a top plan view of the lower disc of the filter paper retainer.

Then upper disc 39 is manually rotated clockwise until the ends of two of its locking feet 51 are firmly engaged under their respective locking ears 56, and the ends of the other two of its locking feet 51 are firmly engaged under their respective locking arms 50, as best seen in FIGS. 6, 9 and 14. Rotation of upper disc 39 is stopped when stops 59 on two of its locking feet 51 (see FIGS. 2, 3 and 9) contact locating pins 42. Two of locking feet 51 have a locking cam 61, as best seen in FIGS. 2, 3, 6 and 9, which act to cam locking arm 50 outwardly into firm engagement with locking ear 56 as upper disc 39 is rotated into its locking position. Locking arms 50, locking lugs 54, locking feet 51 and locking ears 56 are sized and arranged such that when they are firmly engaged with each other, filter paper retainer 18 and lid 24 or base 60 are held tightly together so as to effectuate the desired good seal between filter paper 20 and lid 24 or base 60 which was described above.

Removal of filter paper 20 and retainer 18 is simple and easy. Upper disc 39 is rotated until its locking feet 51 disengage from their respective locking ears 56 and locking arms 50. As has been mentioned, filter paper support pins 40 on lid 24 elevate tabs 32 on filter paper 20. Thus, as the user then starts to push inwardly with his fingers on locking arms 50 of retainer 18 to disengage their locking lugs 54 from locking ears 56 on lid 24, his fingers can easily and automatically trap the filter paper tabs 32 between his fingers and the locking arms 50 of retainer 18. Then when filter paper retainer 18 is lifted away by its locking arms 50, filter paper 20 comes away with it.

Referring now to FIGS. 1 and 2, it is seen that lid 24 and base 60 of the sterilization container system 10 are releasably held in an assembled relation by a pair of latch assemblies 26. Each latch assembly 26 comprises a latch arm 62 rotationally mounted to a release arm 64 with a pivot pin 66 and a spring 68. Release arm 64 is, in turn, rotationally mounted to a bracket 70 with a pair of pivot pins 72; while bracket 70 is, in turn, mounted to lid 24 by a pair of rivets 74.

As seen in FIGS. 1 and 11, when latch assembly 26 is latched, release arm 64 is in a vertical, stowed position, while latch arm 62 engages latch ear 76 on base 60, keeping lid 24 securely in place on base 60. Spring 68 urges latch arm 64 towards latch ear 76 on base 60, thus helping to keep latch arm 64 firmly engaged with latch ear 76 when release arm 64 is in its vertical, stowed position.

Referring to FIGS. 2, 11 and 12, when it is desired to remove lid 24 from base 60, the free end of release arm 64 is rotated outwardly and upwardly about its pivot pins 72. Because of the offset between release arm pivot pins 72 and latch arm pivot pin 66, as the free end of release arm 64 is being so rotated latch arm 62 is disengaged from latch ear 76 on base 60 by first moving downwardly with respect to latch ear 76, and by then moving outwardly with respect to latch ear 76. Such rotation of release arm 64 is stopped by release arm 64 contacting bracket 70 as seen in FIG. 12, enabling the pair of release arms 64 to then be used as handles by which lid 24 can be securely and easily raised, lowered and manipulated by the user.

Although spring 68 does urge latch arm 62 away from release arm 64 and towards latch ear 76 on base 60, spring 68 is configured so that when spring 68 is in an unbiased condition the maximum angular displacement it permits between latch arm 62 and release arm 64 is as seen in FIG. 12, since ends 78, 80 of spring 68 are welded to latch arm 62 and release arm 64, respectively.

When it is desired to secure lid 24 in place on base 60, release arm 64 is rotated downwardly until it is in its vertical, stowed position. As release arm 64 is being so rotated latch arm 62 is first rotated against latch ear 76 on base 60 and then pulls upwardly on latch ear 76 even after it firmly engages latch ear 76. Because of the construction and operation described for latch assembly 76, once release arm 64 reaches its vertical, stowed position as seen in FIG. 11, it will firmly remain in that position unless the free end of release arm 64 is urged outwardly. Latch assembly 26 is configured such that when it is fully latched, gasket 16 is urged into firm, sealing contact with the top of the inner wall 82 of base 60, as seen in FIG. 13. This seal helps keep sterilized instruments stored inside sterilization container system 10 sterile until needed, and helps keep any soiled instruments stored inside sterilization container system 10 after surgery from contaminating the area outside sterilization container system 10 until they can be cleaned and re-sterilized.

Figure 3:
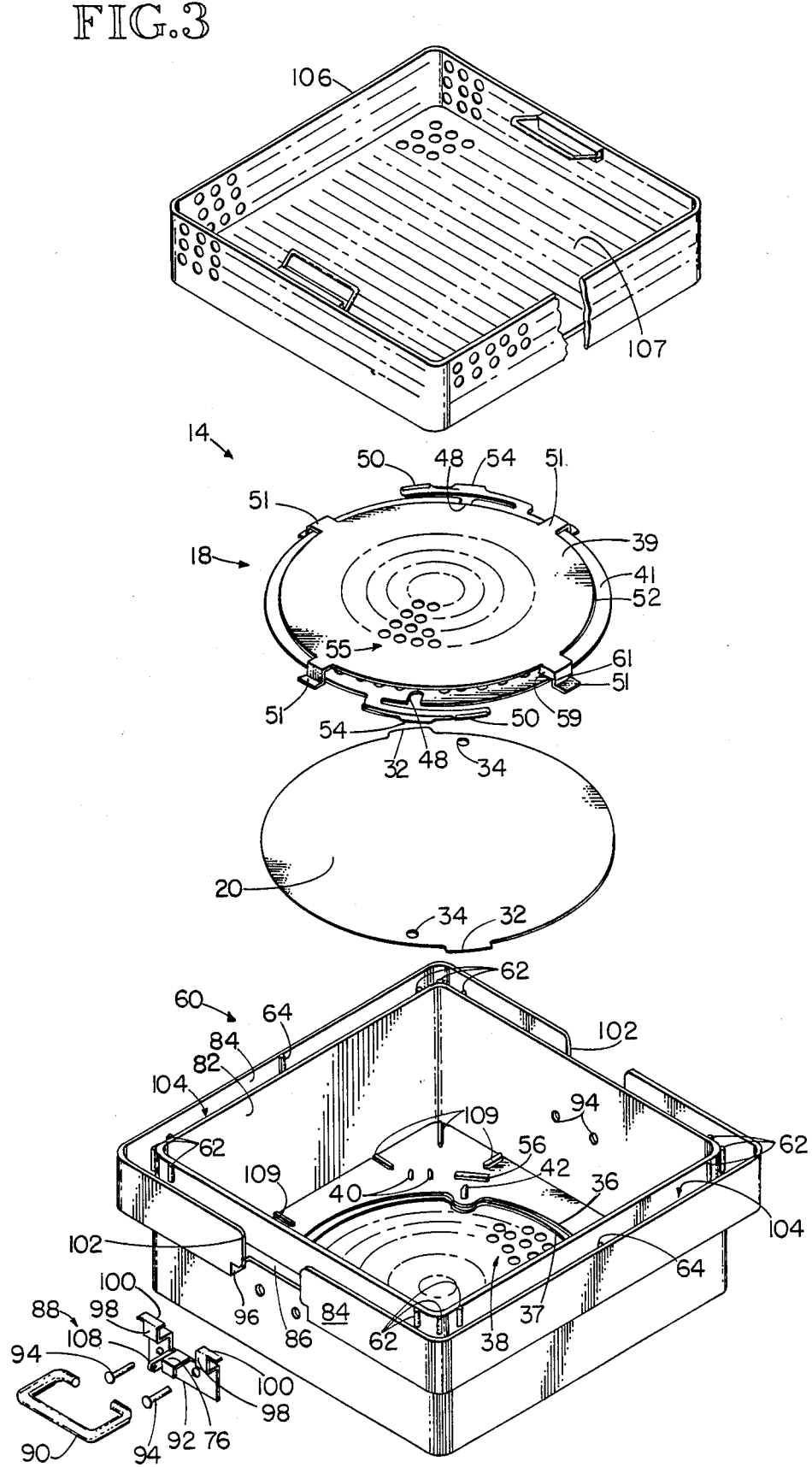
FIG. 3 is an exploded perspective view of its base assembly.

As best seen in FIGS. 3 and 13, the inner and outer walls 82, 84 of base 60 are provided with a plurality of alignment cams 62, 64 which engage wall 23 of lid 24 to ensure lid gasket 16 and the inner wall 82 of base 60 are properly aligned, as seen, when lid 24 is secured in place on base 60 with latches 88.

Turning now to FIG. 3, the base assembly 14 of the sterilization container system 10 is illustrated. Those components of base assembly 14 which are the same as those of lid assembly 12 have been given the same reference numerals for clarity. Thus, base assembly 14 has a filter paper retainer 18, a filter paper 20, vents 38, filter paper sealing flanges (container sealing flange means) 36, 37, alignment pins 42, and locking ears 56 which are the same in all respects as the corresponding elements of the lid assembly 12 described above.

Each of the two base handle assemblies 88 comprise a handle 90 rotatably secured to base 60 by a handle bracket 92 which is secured to inner wall 82 of base 60 by a pair of rivets 94. As seen in FIGS. 1 and 3, when handle bracket 92 is secured to inner wall 80 of base 60 in recess 96 the tops of its handle retaining ears 98 are adjacent the bottom of base flange 86 and retain the free ends of handle 90. Due to such construction, handles 90 assume the vertical, stowage position seen in FIG. 1 under the force of gravity. Handles 90 are rotated upwardly and outwardly by the user to their position shown in FIG. 5 for carrying sterilization container system 10. Handles 90 are prevented from rotating past a right angle with respect to inner wall 82 of base 60 by stops 100 on handle brackets 92.

As seen in FIGS. 3 and 13, base 60 of sterilization container system 10 has an inner wall 82, and an outer protective wall 84 which are joined by a flange 86 which encircles inner wall 82. As seen in the figures, elements 82, 84, 86 preferably have a cross-sectional configuration generally that of an I-beam, to give base 60 strength and rigidity. Flange 86 and outer protective wall 84 help to make base 60 stronger and more rigid. Outer wall 84 helps prevent non-sterile objects from accidentally contacting sterile inner wall 82. The top of outer protective wall 84 is preferably made lower than the top of inner wall 82 of base 60 to reduce the chance that a sterile object being removed from the sterilization container system 10 might contact the non-sterile top of outer wall 84 and thus possibly be contaminated.

Referring again to FIG. 13, when lid 24 is assembled to base 60, the top of the inner wall 82 of base 60 makes a tight sealing contact with gasket 16, as has been described; while the top portion of the base's outer protective wall 84 extends into outer channel 29 of lid 24 where it is, in turn, protected by outer wall 27 of lid 24. Outer wall 23 of gasket channel 28 fits into channel 104 defined between inner and outer walls 82, 84 of base 60. Latch assemblies 26 and latch recesses 25 of lid 24 (seen in FIG. 2) are received in base recesses 102 (seen in FIG. 3).

When using the sterilization container system 10, first filter paper 20 are sealed to the inside of lid 24 and base 60 over vents 38 therein by use of filter paper retainers 18, in the manner previously described. Next, the surgical instruments to be sterilized are placed in the base 60 of sterilization container system 10, preferably by first putting them in a completely perforated stainless steel basket 106 (see FIG. 3) which is then placed in base 60 on top of the installed filter paper retainer 18. As best seen in FIG. 3 the base 107 of basket 106 is elevated, so that the bottom of basket 106 does not contact the upper disc 39 of the filter paper retainer 18 in base 60. This is so the base 107 of basket 106 does not interfere with the free movement of the sterilizing media from the filter paper retainer 18 into the interior of the sterilization container system 10. In addition, base 60 is provided with a plurality of support feet 109 spaced about the inner periphery of inner wall 82 which support basket 106 clear of the bottom of base 60. This is to prevent basket 60 from trapping condensation within the sterilization container system 10 when steam is utilized as the sterilizing media.

Lid 24 is then sealed on top of base 60, in the manner previously described, by use of latch assemblies 26. The sealed sterilization container system 10 is then subjected to any conventional sterilizing procedure, and indicator material 22 or indicator area 22a confirms, as by a color change, that the sealed sterilization container system 10 was properly sterilized.

Since the sterilization container system 10 is sealed, once it and its contents have been sterilized, its contents remain sterilized until the sterilization container system 10 is opened. Preferably, handle bracket 92 has a projecting apertured safety ear 108 which extends through a safety slot 110 in release arm 64, when release arm 64 is in its vertical, stowed position. This permits the insertion of any conventional safety seal 112 through apertured safety ear 108, as seen in FIG. 1, after sterilization container system 10 has been sterilized. Thus, until the safety seals 112 are broken and removed, the lid's latch release arms 64 cannot be opened, and the contents of the sterilization container system 10 remain sterile. Naturally, if a sterilization container system 10 is examined and its safety seals 112 are found to be broken or missing, it should be presumed its contents are no longer sterile, for safety's sake.

After the sterilization container system 10 has been used, the old filter papers 20 are removed and discarded in the manner previously described.

For a sterilization container system 10, which is about 3¾ inches thick when assembled, whose base's inner wall 82 is about 11 inches on a side, and which is being sterilized by a conventional steam sterilization process, the vents 38 in its filter paper retainers 18, lid 24 and base 60 may comprise a circular array of about 494 round holes, each about 3/16th inches in diameter, which have a combined open area of about 27.6 square inches. It is preferred, for maximum flow of this sterilizing media through the sterilization container system 10 during the sterilization procedure that the vents 52 in the lower disc 41 of filter paper retainers 18, lid 24 and base 60 be aligned when retainers 18 are assembled to lid 24 and base 60. Since it is preferred that basket 106 is completely perforated, as has been mentioned, basket 106 does not interfere with the sterilizing media easily reaching the surgical instruments held by basket 106.

Preferably lid latch assemblies 26 and base handle assemblies 88 are made from stainless steel; while filter paper retainers 18, lid 24 and base 60 are injection moulded from any strong, crack resistant, durable plastic compatable with the contemplated sterilization procedure, such as P-1404 Noryl or P-101 polycarbonate made by the General Electric Co., located in Pittsburg, Pa.

Figure 4:
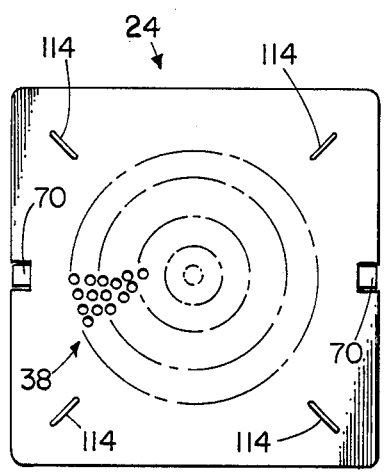
FIG. 4 is a top plan view of FIG. 1.
Figure 5:
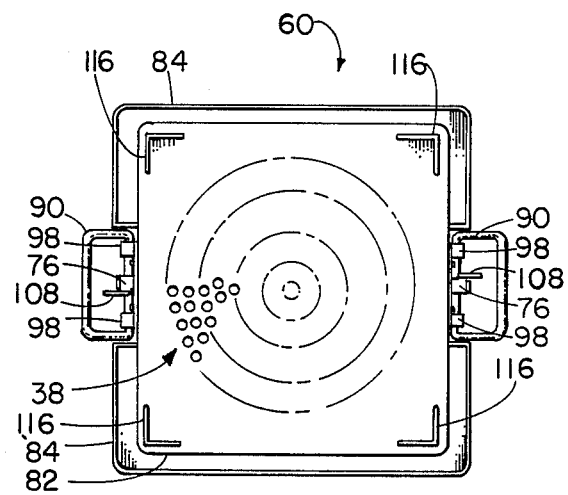
FIG. 5 is a bottom plan view of the base of the sterilization container system, with the carrying handles of the system shown extended.

Stacking of several sterilization container systems on top of each other is aided by lid stacking angles 114 which are adapted to mate with corresponding base corner stacking angles 116, as seen in FIGS. 1, 4 and 5.

In view of the disclosures herein, various further adaptations, modifications, and uses of the sterilization container system 10 of the present invention will now be apparent to those in the art to which it pertains, within the scope of the claims appended hereto; it being understood that all of the descriptions and illustrations contained herein regarding the present invention are strictly by way of non-limiting example.

What is claimed is:

1. A sterilization container system adapted to hold at least one object while the at least one object is being sterilized by a sterilizing fluid medium, wherein said sterilization container system comprises:

a base means;

a lid means;

latch means for releasably securing said lid means to said base means;

a sterilizing chamber means defined within said lid means and said base means when said lid means and said base means are secured together, wherein said chamber means are for holding the at least one object to be sterilized therein;

vent means in at least one of said lid means and said base means, wherein each said vent means is for permitting the sterilizing fluid medium to flow through said sterilizing chamber means to sterilize the at least one object which is held therein;

a respective vent filter means for each said vent means, wherein said respective vent filter means is for preventing microorganisms from reaching the at least one object held in said chamber means through a respective said vent means, and wherein said respective vent filter means includes a respective filter means which is pervious to the sterilizing fluid medium and which is impervious to microorganisms;

a chamber seal means for providing a microorganism proof seal between said lid means and said base means when said lid means and said base means are secured together by said latch means;

wherein said respective vent filter means further comprises:

a respective filter retainer means for releasably securing said respective filter means to a respective one of said lid means and said base means;

filter retainer locking means for releasably securing said respective filter retainer means to said respective one of said lid means and said base means;

at least one chamber sealing flange means on said respective one of said lid means and said base means; and at least one filter retainer sealing flange means on said respective filter retainer means;

wherein when said respective filter retainer means is secured to said respective one of said lid means and said base means, a portion of said respective filter means is tightly sandwiched between said at least one chamber sealing flnge means and said at least one filter retainer sealing flange means to provide a microorganism proof seal between said respective filter means and said at least one chamber sealing flange means on said respective one of said lid means and said base means;

wherein said respective filter retainer means includes filter retainer vent means for permitting the sterilizing fluid medium to freely flow through said respective filter retainer means;
wherein said filter retainer locking means comprise:
a first pair of locking ear means on said respective one of said lid means and said base means; and
a pair of filter retainer locking arm means on said respective filter retainer means;
wherein each said filter retainer locking arm means is resiliently connected to said respective filter retainer means so help ensure that a portion of each said filter retainer locking arm means is resiliently urged into engagement with a respective one of said locking ear means when said respective filter retainer means is secured to said respective one of said lid means and said base means;
wherein said respective filter means further comprises tab means; and
wherein said respective one of said lid means and said base means further comprises means for supporting said tab means in an elevated position near a free end of each of said locking arm means with a portion of said tab means extending past said respective filter retainer means so that when said free ends of said locking arm means are pressed to disengage said locking arm means from said locking ear means, said tap means can easily and selectively be trapped to easily and conveniently remove said respective filter means simultaneously with said respective filter retainer means.

2. A sterilization container system adapted to hold at least one object while the at least one object is being sterilized by a sterilizing fluid medium, wherein said sterilization container system comprises:
a base means;
a lid means;
latch means for releasably securing said lid means to said base means;
a sterilizing chamber means defined within said lid means and said base means when said lid means and said base means are secured together, wherein said chamber means are for holding the at least one object to be sterilized therein;
vent means in at least one of said lid means and said base means, wherein each said vent means is for permitting the sterilizing fluid medium to flow through said sterilizing chamber means to sterilize the at least one object which is held therein;
a respective vent filter means for each said vent means, wherein said respective vent filter means is for preventing microorganisms from reaching the at least one object held in said chamber means through a respective said vent means, and wherein said respective vent filter means includes a respective filter means which is pervious to the sterilizing fluid medium and which is impervious to microorganisms; and
a chamber seal means for providing a microorganism proof seal between said lid means and said base means when said lid means and said base means are secured together by said latch means;
wherein said base means comprises:
a base member;
a peripheral base inner side wall means which extend upwardly from said base member and which has an upper edge; and
a peripheral base outer protective side wall means having an upper edge, wherein said upper edge of said base outer protective side wall means is spaced away from said upper edge of said base inner side wall means, wherein said base outer protective side wall means is supported by said base inner side wall means;
wherein said chamber seal means comprises a peripheral gasket carried by said lid means; wherein when said lid means and said base means are assembled together said gasket is constructed and arranged to seal against said upper edge of said base inner side wall means;
wherein said lid means includes a top lid portion having lid outer protective side wall means formed thereon which extends laterally outwardly past and which is spaced laterally away from said base outer protective side wall means, and wherein a lower edge of said lid outer protective side wall means extends down past said upper edge of said base outer protective side wall means to enable said lid outer protective side wall means to protect an upper edge portion of said base outer protective side wall means;
wherein said base outer protective side wall means extends at least substantially around said base inner side wall means to help protect said upper edge of said base inner side wall means from being contaminated when said lid means is removed from said base means; and
wherein said upper edge of said outer protective side wall means is lower than said upper edge of said inner side wall means to help prevent the at least one object held in said chamber from being contaminated by touching said upper edge of said outer protective side wall means when the at least one object is removed from said base means.

3. A sterilization container system adapted to hold at least one object while the at least one object is being sterilized by a sterilizing fluid medium, wherein said sterilization container system comprises:
a base means;
a lid means;
latch means for releasably securing said lid means to said base means;
a sterilizing chamber means defined within said lid means and said base means when said lid means and said base means are secured together, wherein said chamber means are for holding the at least one object to be sterilized therein;
vent means in at least one of said lid means and said base means, wherein each said vent means is for permitting the sterilizing fluid medium to flow through said sterilizing chamber means to sterilize the at least one object which is held therein;
a respective vent filter means for each said vent means, wherein said respective vent filter means is for preventing microorganisms from reaching the at least one object held in said chamber means through a respective said vent means, and wherein said respective vent filter means includes a respective filter means which is pervious to the sterilizing fluid medium and which is impervious to microorganisms; and
a chamber seal means for providing a microorganism proof seal between said lid means and said base means when said lid means and said base means are secured together by said latch means;
wherein said respective vent filter means further comprises:

a respective filter retainer means for releasably securing said respective filter means to a respective one of said lid means and said base means;
filter retainer locking means for releasably securing said respective filter retainer means to said respective one of said lid means and said base means;
at least one chamber sealing flange means on said respective one of said lid means and said base means; and
at least one filter retainer sealing flange means on said respective filter retainer means;
wherein said at least one chamber sealing flange means extends outwardly at a right angle with respect to a portion of said respective one of said lid means and said base means to which it is attached, wherein said at least one filter retainer sealing flange means extends outwardly at a right angle with respect to said respective filter retainer means, and wherein when said respective filter retainer means is secured to said respective one of said lid means and said base means, said chamber sealing flange means and said filter retainer sealing flange means extend parallel to each other;
wherein when said respective filter retainer means is secured to said respective one of said lid means and said base means, a portion of said respective filter means is tightly sandwiched between said at least one chamber sealing flange means and said at least one filter retainer sealing flange means to provide a microorganism proof seal between said respective filter means and said at least one chamber sealing flange means on said respective one of said lid means and said base means; and p1 wherein said respective filter retainer means includes filter retainer vent means for permitting the sterilizing fluid medium to freely flow through said respective filter retainer means.

4. The sterilization container system according to claim 3, wherein there are at least two of said container sealing flange means; wherein when said respective filter retainer means is secured to said respective one of said lid means and said base means said at least one filter retainer sealing flange means and said at least two container sealing flange means alternate with each other; and wherein said portion of said respective filter means is tightly sandwiched between said at least two container sealing flange means and said at least one filter retainer sealing flange means to provide said microorganism proof seal between said respective filter means and said at least two chamber sealing flange means on said respective one of said lid means and said base means.

5. The sterilization container system according to claim 3, wherein said filter retainer locking means comprise:
a first pair of locking ear means on said respective one of said lid means and said base means wherein each said locking ear means is generally L-shaped and has a first portion which extends outwardly at a right angle from a portion of said respective one of said lid means and said base means to which it is attached and has a second portion which extends parallel to said portion of said respective one of said lid means and said base means; and
a pair of filter retainer locking arm means on said respective filter retainer means;
wherein each said filter retainer locking arm means has an elongated, arcuate body portion which extends along an outer periphery of said respective filter retainer means and which is resiliently connected to said respective filter retainer means to help ensure that a portion of each said filter retainer locking arm means is automatically resiliently urged into engagement with a respective one of said locking ear means when said respective filter retainer means is secured to said respective one of said lid means and said base means.

6. A sterilization container system adapted to hold at least one object while the at least one object is being sterilized by a sterilizing fluid medium, wherein said sterilization container system comprises:
a base means;
a lid means;
latch means for releasably securing said lid means to said base means;
a sterilizing chamber means defined within said lid means and said base means when said lid means and said base means are secured together, wherein said chamber means are for holding the at least one object to be sterilized therein;
vent means in at least one of said lid means and said base means, wherein each said vent means is for permitting the sterilizing fluid medium to flow through said sterilizing chamber means to sterilize the at least one object which is held therein;
a respective vent filter means for each said vent means, wherein said respective vent filter means is for preventing microorganisms from reaching the at least one object held in said chamber means through a respective said vent means, and wherein said respective vent filter means includes a respective filter means which is pervious to the sterilizing fluid medium and which is impervious to microorganisms; and
a chamber seal means for providing a microorganism proof seal between said lid means and said base means when said lid means and said base means are secured together by said latch means;
wherein said base means comprises:
a base member;
a peripheral base inner side wall means which extends upwardly from said base member and which has an upper edge; and
a peripheral base outer protective side wall means formed integrally with said base inner side wall means and having an upper edge, wherein said upper edge of said base outer protective side wall means is spaced away from said upper edge of said base inner side wall means, wherein said base outer protective side wall means is supported by said base inner side wall means;
wherein said chamber seal means comprises a peripheral gasket carried by said lid means; wherein when said lid means and said base means are assembled together said gasket is constructed and arranged to seal against said upper edge of said base inner side wall means;
wherein said lid means includes a lid outer protective side wall means which extends laterally outwardly past said base outer protective side wall means, and wherein a lower edge of said lid outer protective side wall means extends down past said upper edge of said base outer protective side wall means to enable said lid outer protective side wall means to protect an upper edge portion of said base outer protective side wall means; and wherein said base outer protective side wall means extends at least substantially around said base inner side wall means to help protect said upper edge of said base inner side wall means from being contaminated when said lid means is removed from said base means.

7. The sterilization container system according to claim 6, wherein said base outer protective side wall means comprises a base outer protective side wall and a base peripheral flange which connects said base inner side wall means and said base outer protective side wall; wherein said base outer protective side wall and said base peripheral flange have a cross-sectional configuration generally that of a T to give a peripheral top portion of said base means strength and rigidity; and wherein said base peripheral flange extends out at a right angle with respect to said base inner side wall means and said base outer protective side wall extends parallel to said base inner side wall means.

8. A sterilization container system adapted to hold at least one object while the at least one object is being sterilized by a sterilizing fluid medium, wherein said sterilization container system comprises:
a base means;
a lid means;
latch means for releasably securing said lid means to said base means;
a sterilizing chamber means defined within said lid means and said base means when said lid means and said base means and secured together, wherein said chamber means are for holding the at least one object be sterilized therein;
vent means in at least one of said lid means and said base means, wherein each said vent means is for permitting the sterilizing fluid medium to flow through said sterilizing chamber means to sterilize the at least one object which is held therein;
a respective vent filter means for each said vent means, wherein said respective vent filter means is for preventing microorganisms from reaching the at least one object held in said chamber means through a respective said vent means, and wherein said respective vent filter means includes a respective filter means which is pervious to the sterilizing fluid medium and which is impervious to microorganisms; and
a chamber seal means for providing a microorganism proof seal between said lid means and said base means when said lid means and said base means are secured together by said latch means;
wherein said respective vent filter means further comprises:
a respective filter retainer means for releasably securing said respective filter means to a respective one of said base means and said lid means; wherein said respective filter retainer means comprises an upper filter retainer disc and a lower filter retainer disc which are rotatably secured together by a pivot pin located at a center of each of said upper and lower filter retainer discs; wherein each of said filter retainer discs defines a plurality of vents constructed and arranged to permit the free passage of the sterilizing fluid medium through said filter retainer discs;
lower filter retainer locking means for releasably securing said lower filter retainer disc to said respective one of said base means and said lid means; and
upper filter retainer locking means for selectively permitting and preventing relative rotation of said upper and lower filter retainer discs with respect to each other;
wherein when said lower filter retainer disc is secured to said respective one of said base means and said lid means, said upper filter retainer disc is constructed and arranged to be rotated with respect to said lower filter retainer disc until said upper filter retainer locking means prevents relative rotation between said upper and lower filter retainer discs at which time said vents in said upper and lower filter retainer discs are not aligned to prevent the at least one object being sterilized from passing through said vents in said filter retainer discs and putting a hole in said respective filter means.

9. The sterilization container system according to claim 8, wherein said respective filter retainer means further comprises at least one spacing rib extending radially outwardly with respect to said centers of said upper and lower filter retainer discs and being positioned and arranged to hold said upper and lower filter retainer discs in a spaced relationship; wherein said at least one spacing rib and said upper and lower filter retainer discs define at least one lateral vent which is constructed and arranged to permit the free passage of the sterilizing fluid medium transversely between said filter retainer discs and radially outwardly between said upper and lower filter retainer discs; and wherein said respective one of said lid means and said base means for said respective filter retainer means is sized and shaped so as to permit said free passage of the sterilizing fluid medium radially outwardly from between said filter retainer discs.

10. The sterilization container system according to claim 8, wherein said upper filter retainer locking means comprises at least two locking feet carried by said upper filter retainer disc; wherein each said locking foot carried by said upper filter retainer disc comprises a filter portion extending at a right angle with respect to a flat outer surface of said upper filter retainer disc and a second portion carried by said first portion and extending radially outwardly from said first portion parallel to said flat outer surface of said upper filter retainer disc; and at least two corresponding filter retainer locking ears carried by said respective one of said lid means and said base means; wherein each said filter retainer locking ear comprises a locking ear base extending outwardly at a right angle from an inner surface of said respective one of said lid means and said base means, and a locking ear top extending radially inwardly from said locking ear base parallel to said inner surface of said respective one of said lid means and said base means and wherein when said upper filter retainer disc is rotated so said vents in said upper and lower filter retainer discs are not aligned, each said locking foot is also simultaneously rotated into firm engagement with a respective one of said filter retainer locking ears.

* * * * *